United States Patent [19]

Kilpela et al.

[11] Patent Number: 5,415,658
[45] Date of Patent: May 16, 1995

[54] SURGICAL CABLE LOOP CONNECTOR

[75] Inventors: Thomas S. Kilpela; George J. Iwanski; Matthew N. Songer, all of Marquette, Mich.; Robert J. Songer, Northbrook, Ill.

[73] Assignee: Pioneer Laboratories, Inc., Marquette, Mich.

[21] Appl. No.: 167,542

[22] Filed: Dec. 14, 1993

[51] Int. Cl.⁶ .......................... A61F 2/00; A61F 5/04
[52] U.S. Cl. ..................... 606/57; 606/103; 606/65
[58] Field of Search ............... 606/53, 60, 69–74, 606/86, 103, 105; 24/16 R, 18, 19, 27, 28, 29, 276–278

[56] References Cited

U.S. PATENT DOCUMENTS

| 583,455 | 6/1897 | Bush . | |
|---|---|---|---|
| 702,024 | 6/1902 | Moore | 24/276 |
| 911,071 | 2/1909 | Reichert | 24/276 |
| 2,501,978 | 3/1950 | Wichman . | |
| 3,824,995 | 7/1974 | Getscher et al. . | |
| 3,997,138 | 12/1976 | Crock et al. . | |
| 4,120,298 | 10/1978 | Fixel . | |
| 4,146,022 | 3/1979 | Johnson et al. . | |
| 4,262,391 | 4/1981 | Peash | 24/27 |
| 4,269,180 | 5/1981 | Dall et al. . | |
| 4,439,902 | 4/1984 | Huxtable | 24/278 |
| 4,587,963 | 5/1986 | Leibinger | 606/103 |
| 4,889,110 | 12/1989 | Galline et al. | 606/72 |
| 5,116,340 | 5/1992 | Songer et al. | 606/74 |
| 5,147,360 | 9/1992 | Dubousset | 606/61 |
| 5,176,680 | 1/1993 | Vignaud et al. | 606/61 |
| 5,190,545 | 3/1993 | Corsi et al. | 606/74 |
| 5,242,446 | 9/1993 | Steffee et al. | 606/60 |

FOREIGN PATENT DOCUMENTS

| 340738 | 10/1904 | France | 24/278 |
|---|---|---|---|
| 2911748 | 10/1980 | Germany | 606/74 |
| 3244680 | 6/1984 | Germany | 606/74 |
| 3630138 | 3/1988 | Germany | 606/103 |
| 4212635 | 12/1992 | Germany | 606/69 |

OTHER PUBLICATIONS

The Dall-Miles Trochanter Cable Grip System-Dall Miles JBJS, 1983 vol. 65-B, No. 1:55–59, Clarke, Shea, Bierbaum Corp., 1979, 141:102–10 (13 pages).

Primary Examiner—Stephen C. Pellegrino
Assistant Examiner—Nancy Mulcare
Attorney, Agent, or Firm—Gerstman, Ellis & McMillin, Ltd.

[57] ABSTRACT

A surgical connector for cable comprises a body having a pair of opposed ends and a first side extending between the ends. Outwardly extending projections adjacent the first side and ends may be provided to facilitate securance of the connector in a desired position. Cable-receiving bores extend from each of the ends inwardly toward each other, typically at an obtuse angle of less than 180°. The bores have inner ends that communicate with a central aperture which is open to at least the side of the body which is opposed to the first side. Alternatively, the central aperture may extend entirely through the body and be open to both the first side and the opposed side. Also, a novel retention technique for cable is disclosed, for more general use, if desired.

32 Claims, 2 Drawing Sheets

SURGICAL CABLE LOOP CONNECTOR

BACKGROUND OF THE INVENTION

This invention relates to a surgical cable loop connector which is typically used for the securance of broken bones together, serving as an implant for use in bone surgery.

In orthopedic surgery where severe breaks of bones have taken place, or in reconstructive procedures on bones, for example reconstructive hip procedures or the like, a permanent cable implant is provided to hold bone portions together. For example, during a total hip replacement, press-fit femoral components are inserted into the canal of the femur, resulting in an extremely tight fit in some cases. Seating of these press-fit components has been shown to induce large hoop stresses in the proximal femur, which can result in longitudinal cracks. Thus, in the prior art, a cerclage cable system is provided to apply a counteracting compressive hoop stress, which prevents crack formation and/or propagation.

The existing methods of bone fixation in conditions such as the above include the use of plates and screws, monofilament wire, and cable and crimp systems. Failure of single strand wires due to fracture or loosening has been reported as being quite common. Plates and screws are also provided to attempt to reduce spiral, longitudinal and butterfly fractures, but such an expedient is not very successful with long breaks or where there are multiple bone fragments. Also, too many plates and intrusive screws tend to weaken the resulting bone union.

Existing cable systems of the prior art are bulky and stiff. Also the cable is hard to work with, and the crimp that is used requires special, cumbersome tools for tensioning and crimping. Likewise, the crimping process in many prior art systems is difficult, and must be learned to be effective.

Also, prior art cable loop connectors have exhibited a problem of bone necrosis in areas where the connector contacts the bone. An additional problem of such cable loop connectors is the possibility of slippage along the shaft of the bone after implantation.

Furthermore, with prior art cable loop connectors, the cable as it is implanted may exhibit a sharp angled turn of a few degrees at the point where it exits from an aperture in the cable loop connector, because of the relative position of the bone and the connector, and the direction of the cable passage holes in the connector. This creates a point of focused stress against the cable which can, over time, result in failure of the cable.

Also, in prior art cable loop connectors, the process of crimping to secure the cable loop is a fairly complex one, and which is easily done in improper manner. By this invention, an essentially foolproof technique of cable securance is provided.

Additionally, the cable loops that are provided by this invention may be cable loops which extend less than 360° about a bone from securance point to securance point and occupy a plane transverse to the bone. In the pertinent prior art, the cable loops provided by the prior art connectors are more than 360°, with portions of the looped cable passing by other portions thereof in a spiral manner. This can create an undesirable torsion as such a prior art cable loop is tightened with a connector, which torsion can be eliminated by this invention.

Also, the cable loop connector of this invention is basically foolproof as to which side should be placed against the bone. In prior art systems, errors can be made with respect to that issue. Also, by this invention, securance of the cable may be performed with a single operation using a common hex head screw driver or other simple tool. To the contrary, in the analogous prior art systems two crimping steps must be provided with a special, high cost crimping tool.

DESCRIPTION OF THE INVENTION

By this invention, a surgical connector for cable comprises a body having a pair of opposed ends and a first side extending between the ends. Outwardly extending projections are provided adjacent the first side and ends to facilitate securance of the connector in a desired position. Cable-receiving bores are also provided, extending from each of the ends inwardly toward each other, typically at an obtuse angle of less than 180°. The bores have inner ends that communicate with a central aperture which is open to at least the side of the body which is opposed to the first side, although in some embodiments the entire center of the connector may be open, so that the central aperture is open to both sides of the connector. Means are also provided for securing cable in the bores.

In one embodiment, the first side of the connector can be concave to a sufficient degree that the only contact with the bone upon which the connector rests is at the ends of the connector, for example an adult femur shaft. Particularly, bone contact may be through the projections. The remainder of the connector is preferably spaced from the bone, to reduce the area of contact with the bone and thus to greatly reduce the problem of bone necrosis.

The outwardly extending projections which are adjacent the first side and ends to facilitate securance of the connector typically operate by digging into the bone, being typically sharp-edged or sharp-ended members of a low bone-covering surface area. If desired, for ease of manufacture, the outwardly extending projections may comprise sharp ribs, typically on the edges of the connector, projecting from the first side and extending between the opposed ends. In this circumstance, when the connector body is sufficiently concave, the only typical area of bone contact is at the respective ends of sharp ribs at the ends of the surgical connector, so that the surgical connector is joined to the bone only at typically four points of minimum area contact. At these points the ribs dig in, to secure the cable loop connector in a desired position on the bone, preventing sliding and the like.

It is preferred for the bores defined in the connector to be positioned at an angle, typically an obtuse angle of less than 180°. This permits cable portions to extend straight from the bores in a direction that is substantially tangent to the bone which is surrounded by the cable loop. Thus, the cable is protected from any sharp-angled turn that can focus stress and reduce its useful life.

It is also preferred for the bores to define longitudinal axes which occupy a common plane. In other words, while typically occupying an obtuse angle with each other, the bores are on line with each other without skewed or laterally spaced relationship.

The bores are also preferably free of sharp edges at their ends, by chamfering or the like. The absence of such sharp edges, as created by a radius or otherwise profiled surfaces where the bore exits the connector, provides added protection from focused stress to the cable, to improve its useful life.

At least one of the cable securing means may comprise a transverse, screw-threaded hole typically extending through the connector and which intersects one of the bores. A blunt-tipped, threaded screw is provided, being advanceable into the screw-threaded hole to compress typically a cable/sleeve combination and to retain the cable in the one bore. The blunt tip of the screw typically is not flat in its forward face, but rather is convex but without a point. This focuses a retention force into at least central areas of the cable/sleeve combination, and improves the retention thereof while minimizing strand breakage.

It is preferred for a malleable metal sleeve to be positioned in the one bore having the transverse hole, to surround the cable and to protect it from strand breakage as the screw is advanced, thus defining the cable/sleeve combination. The sleeve is bent and collapsed by the screw during such advancement, which causes strong retention of the cable in the connector.

Also, the above screw may define a rear head to limit screw-threaded advancement of the screw into the one bore. The screw then may be proportioned so that the position of maximum advancement is where the rear head enters into engagement with the connector, so that the screw can be advanced no farther at a predetermined position. This predetermined position of maximum advancement may be proportioned to be the desired position of optimum advancement, for best retention of the cable with minimum cable damage. Thus, no skill, expertise, or measuring is required to secure the cable in the connector. One merely advances the screw until its head bottoms out, and no further advancement is possible. Then the job is done.

The specific cable end retaining members of this invention may also be used with other connector designs, for example in a simple plate, as shown below in another embodiment.

DESCRIPTION OF SPECIFIC EMBODIMENTS

Figure 1:
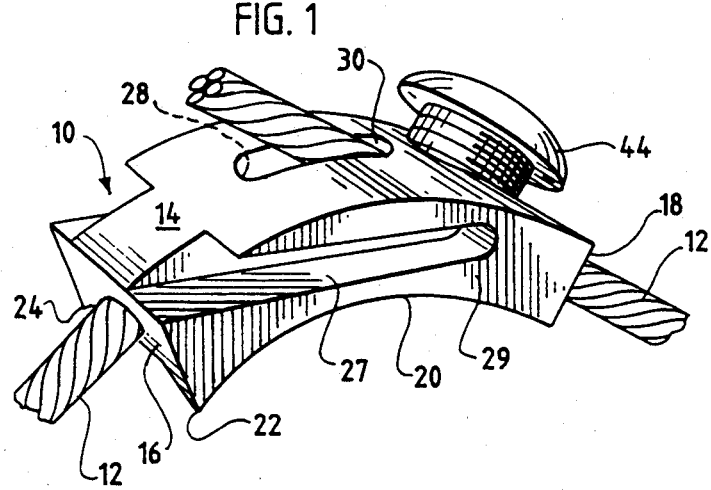
FIG. 1 is a perspective view of the connector for cable ends in accordance with this invention.

Referring to FIGS. 1-4, a surgical connector 10 for a loop of cable 12 is disclosed. Connector 10 comprises a body 14 which has a pair of opposed ends 16, 18, and a first side 20 extending between the ends.

Figure 4:
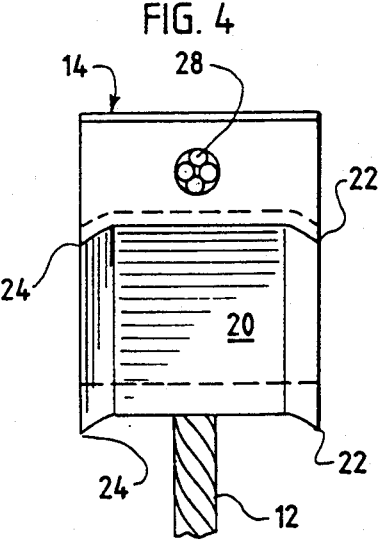
FIG. 4 is a sectional view taken along line 4—4 of FIG. 3.
Figure 3:
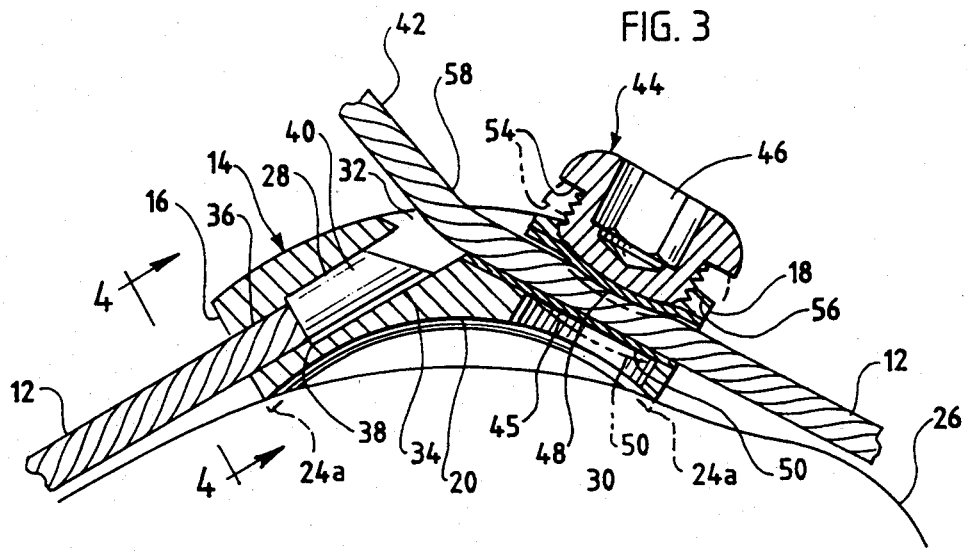
FIG. 3 is a longitudinal sectional view of the connector of FIG. 1, showing its positioning with a cable loop on a portion of a bone of a patient.

As shown particularly in FIGS. 3 and 4, the first side 20 of body 14 is concave in shape. Alternatively, an essentially concave shape may be defined by intersecting, flat sides forming an indentation that is similar in effect to the concave arc shape of side 20 which is specifically shown.

Also, side 20 has a central portion which is indented, and is defined between a pair of sharp ribs 22, 24 which project outwardly from the remainder of side 20. Ribs 22, 24 form projections at their ends (illustrated by reference numeral 24a in FIG. 3), which can dig into the bone 26 upon which surgical connector 10 may be implanted, to prevent sliding of connector 10 about the bone as it retains the loop of cable 12 about bone 26 in tight, bone-retaining relation.

These respective projections 24a etc. which are defined at the ends of sharp ribs 22 are conveniently made simply by cutting out a central portion of side 20 with an appropriate tool to provide the respective ribs 22, 24, even though, typically, only the respective ends of ribs 22, 24 are used for retention of connector 10 in position on a bone 26.

Slots 27 are provided on both sides 29 of body 14 to facilitate engagement of the body with a cable tensioner, for tightening a cable loop formed by connector 10.

Connector body 14 also defines a pair of cable receiving bores 28, 30. As shown particularly in FIG. 3, bore 28 extends from end 16 to an open aperture 32, defined in the side of body 14 which is opposed to side 20. Alternatively, aperture 32 can extend entirely through connector body 14.

Bore 30 extends from end 18 to the same open aperture 32, so that, with the connector of this invention, the cable loop 12 that is formed extends less than 360° between the cable portions secured in connector body 14. Bores 28, 30 define an obtuse angle to each other on the order of 110° to 160°, which permits the portions of cable 12 extending outwardly from ends 16, 18 to extend in a direction that is substantially tangent to the bone 26 surrounded thereby. As previously stated, this reduces the possibility of a sharp-angled bend in cable 12 at either of the ends 16 or 18, which reduces stress on the cable.

Figure 2:
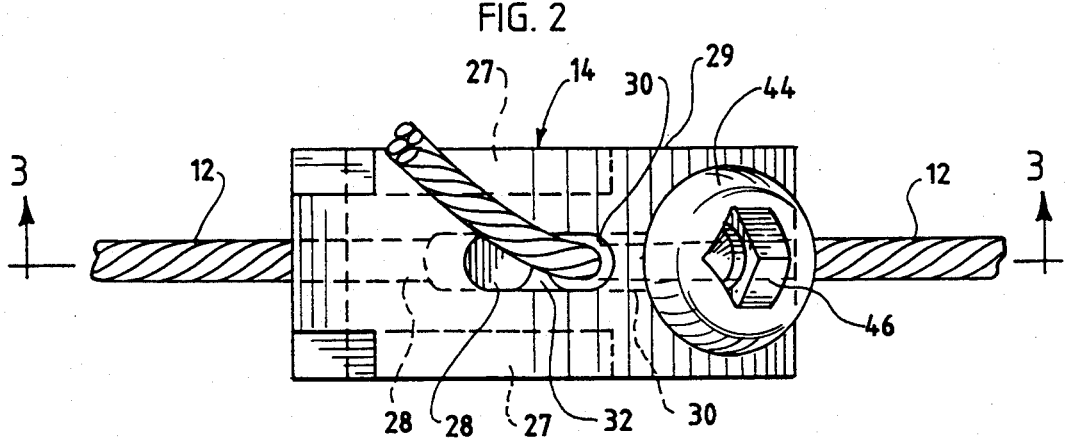
FIG. 2 is a plan view of the connector of FIG. 1.

Also, as shown particularly in FIG. 2, it can be seen that bores 28, 30 define longitudinal axes which occupy a common plane, although they are at an obtuse angle to each other. In the prior art, respective bores of certain connectors are out of a common plane, which causes their cable loops to be laid down in a spiral pattern rather than a substantially planar pattern as in this invention. Such a spiral pattern can create undesired torque on the connector, which may harm the cable.

Also, the respective ends of bores 28, 30, where they exit from ends 16, 18, can be chamfered, radiused, or the like, to be free of cable-cutting, sharp edges. Other edges of connector 10 may be rounded or chamfered in similar manner as desired for similar purposes, and also to avoid tissue trauma of the implant since it is intended for long term implantation.

Bore 28 defines an inner portion 34 which is of larger diameter than an outer bore portion 36, which extends through connector end 16. The two bore portions are separated by an annular step 38.

The end of cable 12 which occupies bore 28 may carry an enlarged tip 40, typically made in conventional manner of metal, which is firmly swaged to the end of cable 12, and which is of enlarged diameter so as to fit into bore portion 34, but not to pass through bore portion 36.

Accordingly, cable 12 may be fed through aperture 32 into bore 28, with cable tip 40 comprising the proximal or rear end thereof, until the cable occupies the position shown in FIG. 3, where it is captured in bore 28 and cannot be pulled outwardly therethrough. Cable 12 may then be brought around bone 26 into a loop, and passed through end 18 and bore 30, as shown. The distal end portion 42 of cable 12 may be pulled in a tensioning device to provide the desired tension to the loop defined by cable 12.

Then, to secure the cable loop, threaded screw 44 may be advanced by a conventional hexagonal screw driver or the like which fits in driving aperture 46 of screw 44. The threaded screw 44 advances through an open hole 45, partly threaded, that communicates transversely with bore 30 through body 14, to provide a compressive, frictional retention of cable 12. Screw 44 can be seen to have a convex, blunt-tipped forward end 48, which compresses a cable/sleeve combination 12, 50 and retains cable 12 and sleeve 50 within bore 30.

Sleeve 50 is made of malleable metal and is provided within bore 30 through which cable 12 extends. Sleeve 50 bends and collapses as shown in dotted lines as screw 44 is advanced into cable retaining configuration. This protects the cable strands from breaking stress due to the rotation of screw 44 as it advances. The deformation of sleeve 50 (in dotted lines) aids in securing the cable 12 in clamped relation with connector body 14.

Alternatively, sleeve 50 and cable 12 may be crushed against a bottom wall of hole 45 rather than hole 45 being open.

By this invention, screw 44 has a head with an annular, flat forward face 54. As screw 44 is advanced, flat face 54 enters into engagement with annular seat 56 surrounding the threaded aperture which screw 44 occupies. Screw 44 is of such a predetermined length so that when annular face 54 presses against seat 56 to terminate the screw-threaded advancement of screw 44, the forward, blunt end 48 of screw 44 is advanced to a predetermined position of optimum advancement for retention of cable 12, where deformation and frictional forces of retention are optimum without significant breakage of strands in the preferably multi-strand cable 12.

Thus, by this invention, a loop of cable 12 can be formed with great ease, and with a single securing advancement of a screw 44, without the need for a torque limiting wrench. The optimum desired position of advancement is automatically predetermined by simply advancing screw 44 with a conventional screwdriver or the like as far as possible, to that point where annular face 54 engages annular seat 56. Then, the cable which has been properly tensioned by a suitable tensioning device, may be cut at a desired point such as point 58, and the cable loop is complete.

Referring to FIGS. 5–8, another embodiment of the invention is disclosed, being simplified in certain respects from the previous embodiment.

Figure 5:
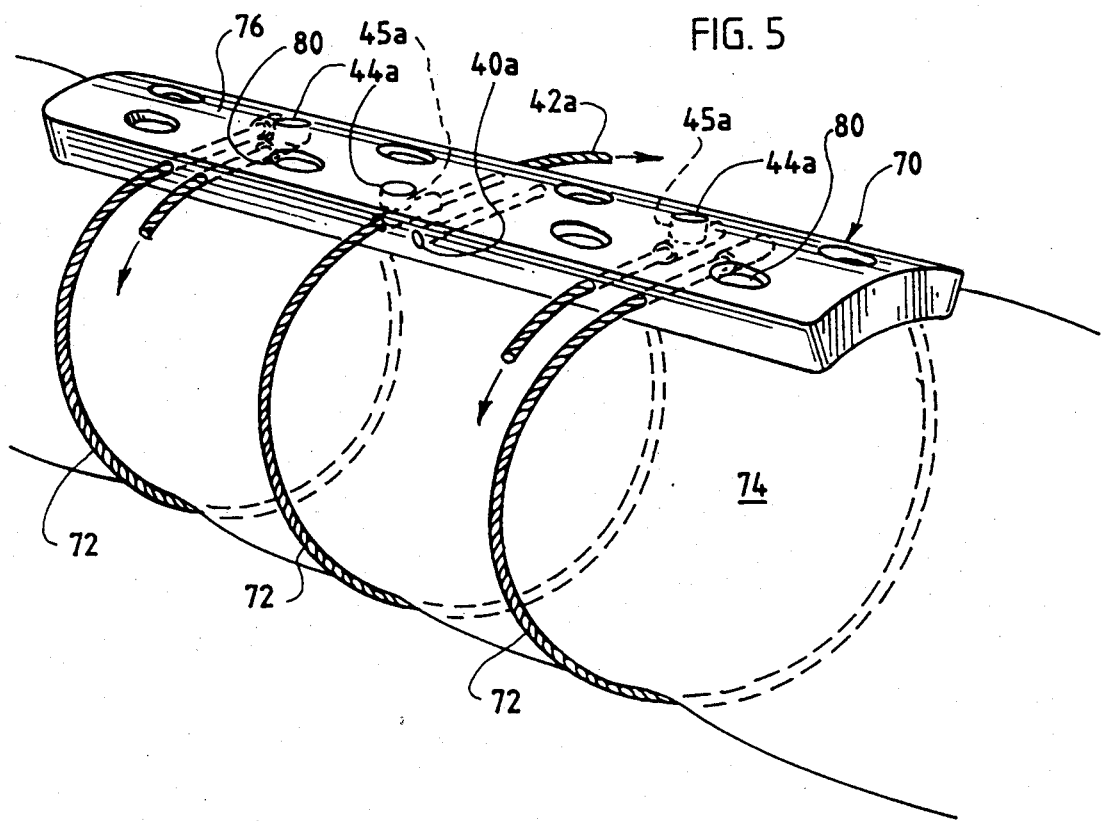
FIG. 5 is a perspective view of another embodiment of a surgical cable loop connector of this invention, serving as a bone plate for supporting and retaining badly broken bones.

FIG. 5 shows a cable clamp 70 for a series of loops of cable 72, for binding and securing a badly broken bone 74, for example.

Cable clamp 70 comprises a body 76 which is basically a flat plate having transverse apertures 80 for bone screws, which may be of conventional fabrication.

Figure 6:
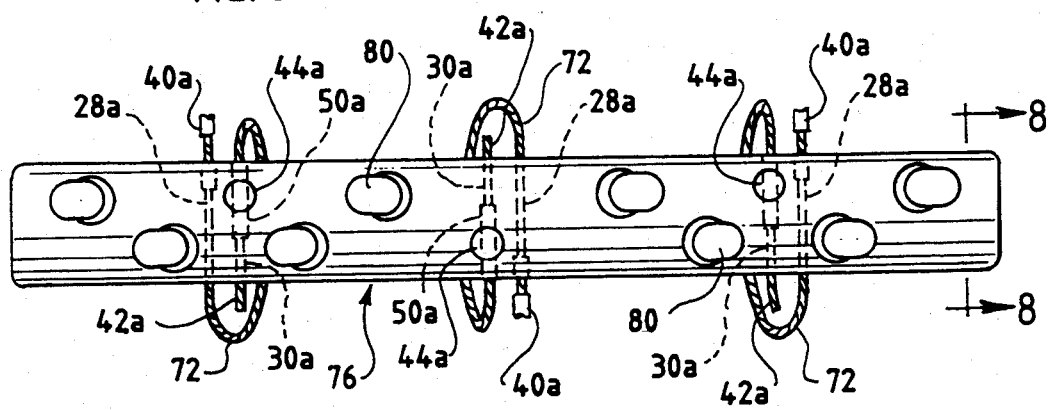
FIG. 6 is a plan view of the bone plate of FIG.
Figure 7:
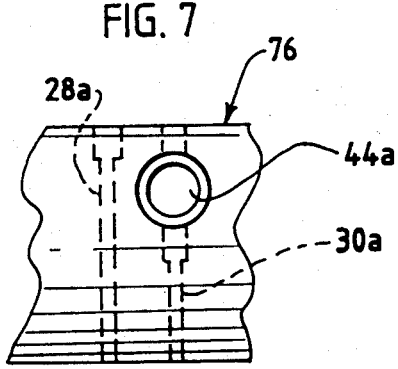
FIG. 7 is an enlarged, fragmentary plan view of a portion of the bone plate of FIG. 6.

In accordance with this invention the respective cable loops are retained by plate 76 adjacent their ends by a system which is essentially similar to the retention means of the previous embodiment. Specifically, at each end of each cable 72 that is being formed into the loop is an enlargement 40a that is typically similar to enlarged cable tip 40 of the previous embodiment, swaged to the cable end, and functioning in a manner similar to the previous embodiment. Thus, bar-like body 76 defines a lateral bore 28a for each cable loop 72, as shown in FIG. 6, which is of identical shape to bore 28 of the previous embodiment, and which retains cable end 40a in a similar manner.

Body 76 also defines another set of lateral bores 30a which extend transversely through plate-like body 76 and which are parallel to lateral bores 28a. Bores 38a are similar in structure and function to bore 30 of the previous embodiment, being shown to be receiving the other end of cable loop 72 from the end defining enlarged tip 40a. As in the previous embodiment, each cable loop 72 is wrapped around a bone and tightened by tightening the respective cable ends 42a, using any desired tensioning device. Then, screw 44a, which is similar to screw 44 of the previous embodiment, is tightened into a hole 45a which intersects bore 30a in a manner which may be identical to the structure and functioning of the corresponding structure 30, 44, 45 of the previous embodiment, for reliable and effective cable retention, preferably, without cable strand breakage. Particularly, it is preferred to include a malleable metal sleeve 50a through which each cable passes and which is deformed and collapsed by screw 44a, in a manner of functioning identical to that of the prior art.

Figure 8:
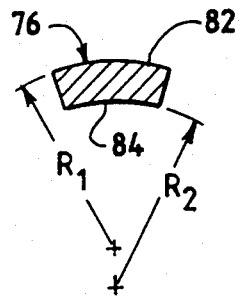
FIG. 8 is a sectional view taken along line 8—8 of FIG. 6.

FIG. 8 discloses a transverse sectional view of body 76. As shown, body 76 may have top and bottom faces 82, 84 which define transverse arcs of a radius R1 and R2 respectively. It is generally preferred for R1 and R2 to be substantially the same radius. For example, 1.125 inch. Also, the width of body 76 may be about 0.7 inch, and its length may be about 6 inches. It can be seen from FIG. 5 that body 76 is straight in its longest dimension, perpendicular to the dimension of the transverse arcs defined in sides 82, 84.

The cable loop connector of FIGS. 5 through 8 provides multiple cable loops arranged in a line, for the support of bones which are broken in a complex, serious manner and the like, serving as an alternative to the cable connector of FIGS. 1 through 4. These cable loop connectors have significant advantages over the prior art cable loop connectors, as described herein.

The above has been offered for illustrative purposes only, and is not intended to limit the scope of the invention of this application, which is as defined in the claims below.

That which is claimed is:

1. A surgical connector for cable which comprises a body having a pair of opposed ends and a first side extending between said ends; outwardly extending projections adjacent said first side and ends to facilitate securance of said connector in a desired position, said outwardly extending projections comprising sharp ribs projecting from edges adjacent said first side and extending between the opposed ends, whereby bone contact is through ends of said sharp ribs; cable-receiving bores extending from each of said ends inwardly toward each other at an obtuse angle of less than 180°, said bores having inner ends that communicate with a central aperture open to at least the side of said body which is opposed to said first side, for securing lengths of cable in said bores.

2. The connector of claim 1 in which said first side is concave.

3. The connector of claim 1 which is for retention of a cable loop for bone retention, the bores being positioned at an obtuse angle that permits cable portions to extend straight from the bores in a direction that is substantially tangent to the bone surrounded by the cable loop.

4. The connector of claim 1 in which said bores define longitudinal axes which occupy a common plane.

5. The connector of claim 1 in which said bores define ends that are free of sharp edges.

6. The connector of claim 1 in combination with a cable in which said cable is secured in one of said bores by a transverse, screw-threaded hole intersecting said one bore, and a screw advanceable therein to compress and retain the cable in said one bore.

7. The connector of claim 6 in which said screw defines a rear head to limit screw-threaded advancement of said screw into the one bore, the screw being proportioned whereby the position of maximum screw advancement is the position of optimum advancement for retention of said cable.

8. The connector of claim 7 in which a malleable metal sleeve is positioned in said one bore to surround said cable in the one bore and to be collapsed by said screw.

9. The connector of claim 6 in which a malleable metal sleeve is positioned in said one bore to surround said cable in the one bore and to be collapsed by said screw.

10. The connector of claim 6 in combination with a cable, which connector carries said cable in both of said cable-receiving bores to define a cable loop, said cable having an end which defines a transversely enlarged portion, said second cable-receiving bore defining an enlarged diameter inner portion receiving said transversely enlarged cable portion, and a reduced-diameter outer portion, to retain said cable and to prevent its outward movement through the reduced-diameter outer bore portion.

11. The connector or claim 1 in combination with a cable, which connector carries a length of cable in both of said cable-receiving bores which defines a loop, said cable having an end which defines a transversely enlarged portion, said second cable-receiving bore defining an enlarged diameter inner portion receiving said transversely enlarged cable portion, and a reduced-diameter outer portion, to retain said cable and to prevent its outward movement through the reduced-diameter outer bore portion.

12. A surgical connector for cable ends in combination with lengths of cable, which connector comprises a body having a pair of opposed ends, and a concave first side extending between said ends; sharp ribs projecting from said first side and extending between the opposed ends to define outwardly extending projections adjacent said first side and opposed ends, to facilitate securance of said connector in a desired position; cable-receiving bores extending from each of said ends inwardly toward each other at an obtuse angle of less than 180°, said bores having inner ends that communicate with a central aperture open to at least the side of the body which is opposed to said first side, said lengths of cable being secured in said bores.

13. The connector of claim 12 which carries a cable loop for bone retention, the bores being positioned at an obtuse angle that permits cable portions to extend straight from the bores in a direction that is substantially tangent to the bone surrounded by the cable loop.

14. The connector of claim 13 in which said bores define longitudinal axes which occupy a common plane.

15. The connector of claim 14 in which one length of said cable is secured in one of said bores by means of a transverse, screw-threaded hole intersecting said one bore and a blunt-tipped screw advanceable therein to compress and retain said cable in said one bore.

16. The connector of claim 15 in which a malleable metal sleeve is positioned in said one bore to surround said cable in the one bore and to be collapsed by said screw.

17. The connector of claim 16 in which said screw defines a rear head to limit screw-threaded advancement of said screw into the one bore, the screw being proportioned whereby the position of maximum screw advancement is the position of optimum advancement for retention of the cable.

18. The connector of claim 16 in which a second of said cable-receiving bores carries an end of said cable, which cable end is enlarged, said second cable-receiving bore defining an enlarged diameter inner portion receiving said enlarged end, and a reduced-diameter outer bore portion to retain said cable and to prevent its outward movement through the opposed end associated with said second bore.

19. A surgical connector in combination with a cable, said surgical connector comprising a body having a pair of opposed ends and a first side extending between the ends; outwardly extending projections adjacent said first side and ends to facilitate securance of said connector in a desired position; cable-receiving bores extending from each of said ends inwardly toward each other at an obtuse angle of less than 180°, said bores having inner ends that communicate with a central aperture open to at least the side of said body which is opposed to said first side, said cable being secured in one of said bores by a transverse, screw-threaded hole intersecting said one bore, and a screw advanceable in said hole to compress and secure the cable in said one bore.

20. The connector of claim 19 in which said screw defines a rear head to limit screw-threaded advancement of said screw into the one bore, the screw being proportioned whereby the position of maximum screw advancement is the position of optimum advancement for retention of said cable.

21. The connector of claim 20 in which a malleable metal sleeve is positioned in said one bore to surround said cable in the one bore and to be collapsed by said screw.

22. A surgical connector for cable in combination with lengths of cable, which connector comprises a body having a pair of opposed ends and a first side extending between said ends; cable receiving bores extending from each of said ends inwardly toward each other at an obtuse angle of less than 180°, said bores having inner ends that communicate with a central aperture open to at least the side of said body which is opposed to said first side, said lengths of cable being secured in said bores, said first side being longitudinally concave of a radius smaller than that of an adult femur shaft whereby said connector can rest on an adult femur shaft with the opposed ends of said connector in contact with said femur shaft and the remainder of said first side being spaced from said femur shaft.

23. The connector of claim 22 in which said bores define longitudinal axes which occupy a common plane, said lengths of cable secured in said bores comprising part of a loop of cable of less than 360°.

24. The connector of claim 22 in which said screw defines a rear head to limit screw-threaded advancement of said screw into the one bore, the screw being proportioned whereby the position of maximum screw advancement is the position of optimum advancement for retention of said cable.

25. The connector of claim 24 which carries a length of cable in both of said cable-receiving bores which defines a loop, a second of said cable-receiving bores carrying a transversely enlarged portion, said second cable-receiving bore defining an enlarged diameter inner portion receiving said enlarged cable portion, and a reduced-diameter outer portion to retain said cable and to prevent its outward movement through the reduced-diameter outer bore portion and the opposed end associated with said second bore.

26. A surgical cable connector which comprises a body, a first cable receiving bore defined in said body, and securing means for retaining cable in secured manner within said bore comprising a transverse, screw-threaded hole intersecting said bore; a malleable sleeve occupying said bore and extending completely across said hole in bridging relation, and a screw rotatably mounted in said hole, whereby a cable extending through said sleeve in said bore may be bent with said sleeve by the advancing screw into a cable-retaining, clamped condition.

27. The connector of claim 26 in which said hole extends completely through said body.

28. The connector of claim 27 in which said screw defines a rear head to limit screw-threaded advancement of said screw into the bore, the screw being proportioned whereby the position of maximum screw advancement is the position of optimum advancement for retention of said cable.

29. The connector of claim 28 which defines a second cable-receiving bore and which carries a length of cable in both of said cable-receiving bores which defines a loop, said cable having an end which defines a transversely enlarged portion, said second cable-receiving bore defining an enlarged diameter inner portion receiving said transversely enlarged cable portion, and a reduced-diameter outer portion, to retain said cable and to prevent its outward movement through the reduced-diameter outer bore portion.

30. The connector of claim 26 in which said screw defines a rear head to limit screw-threaded advancement of said screw into the bore, the screw being proportioned whereby the position of maximum screw advancement is the position of optimum advancement for retention of said cable.

31. The connector of claim 26 which defines a second cable-receiving bore and which carries a length of cable in both of said cable-receiving bores which defines a loop, said cable having an end which defines a transversely enlarged portion, said second cable-receiving bore defining an enlarged diameter inner portion receiving said transversely enlarged cable portion, and a reduced-diameter outer portion, to retain said cable and to prevent its outward movement through the reduced-diameter outer bore portion.

32. The connector of claim 26 in which said body comprises a plate which carries a plurality of said securing means for retaining a plurality of said cables.

* * * * *